United States Patent [19]

Collins

[11] 4,051,845

[45] Oct. 4, 1977

[54] DRAPE ASSEMBLY WITH POUCH AND METHOD

[75] Inventor: Robert F. Collins, Barrington, Ill.

[73] Assignee: The Kendall Company, Boston, Mass.

[21] Appl. No.: 683,568

[22] Filed: May 5, 1976

Related U.S. Application Data

[63] Continuation-in-part of Ser. No. 664,136, March 5, 1976.

[51] Int. Cl.² .............................................. A61B 19/06
[52] U.S. Cl. ................................................ 128/132 D
[58] Field of Search .................. 128/132 D, 292, 275, 128/227; 206/440, 460, 813

[56] References Cited

U.S. PATENT DOCUMENTS

| | | | |
|---|---|---|---|
| 3,452,750 | 7/1969 | Blanford | 128/132 D |
| 3,494,356 | 2/1970 | Melges | 128/292 X |
| 3,561,670 | 2/1971 | Segal et al. | 206/813 X |
| 3,693,618 | 9/1972 | Madden | 128/132 D |
| 3,791,382 | 2/1974 | Collins | 128/132 D |
| 3,889,667 | 6/1975 | Collins | 128/132 D |

Primary Examiner—Lawrence W. Trapp
Attorney, Agent, or Firm—Powell L. Sprunger

[57] ABSTRACT

A drape assembly comprising, a sterile drape, and a retaining pouch which may be attached to the drape. The pouch has a pocket for retaining refuse discarded pursuant to an operation.

16 Claims, 34 Drawing Figures

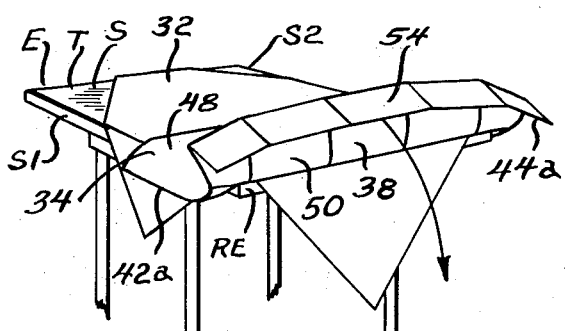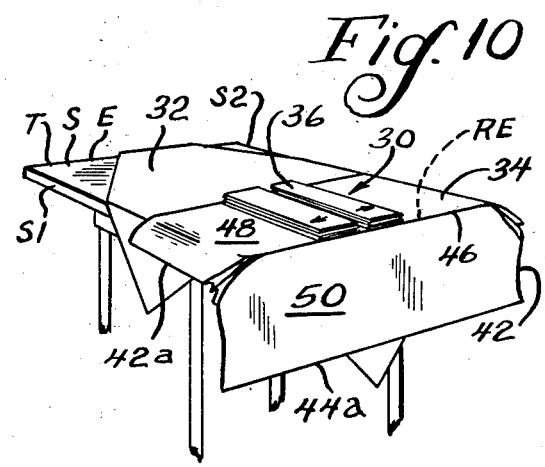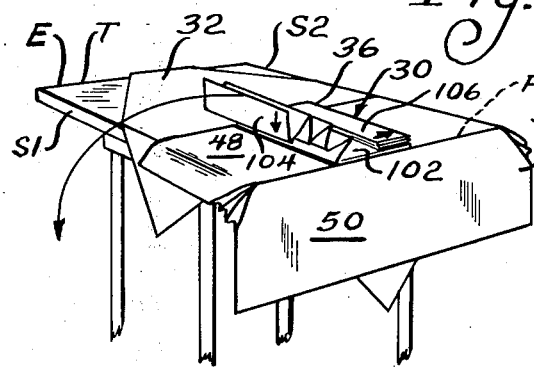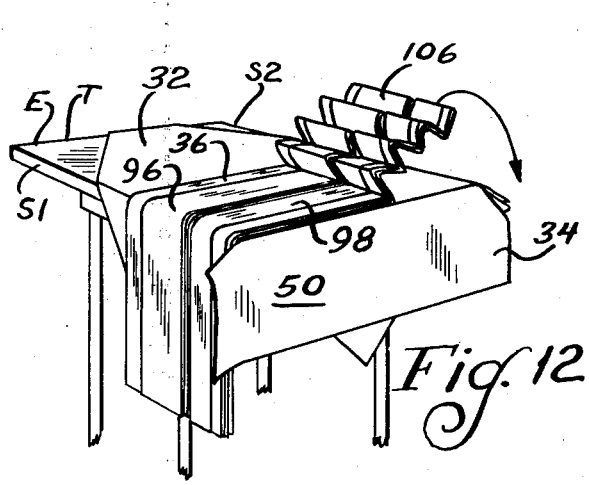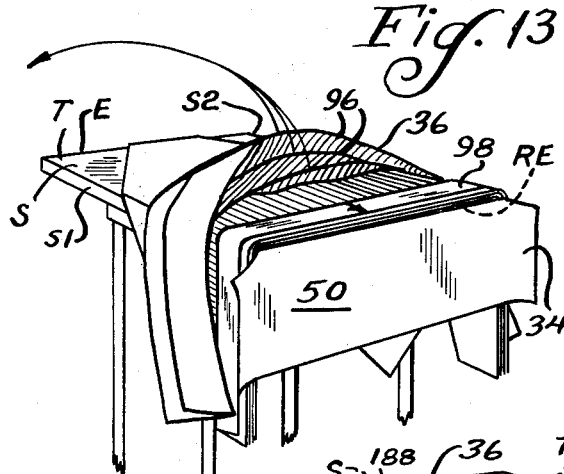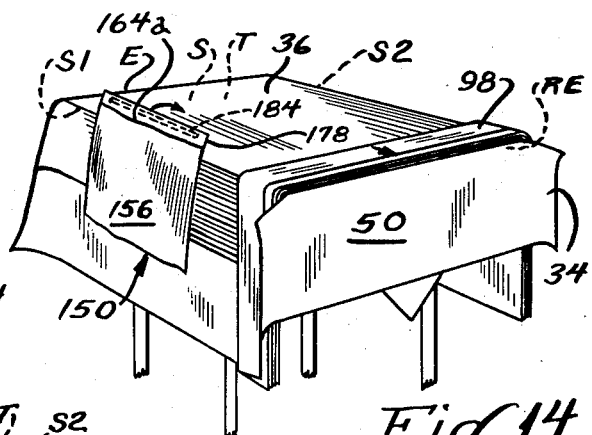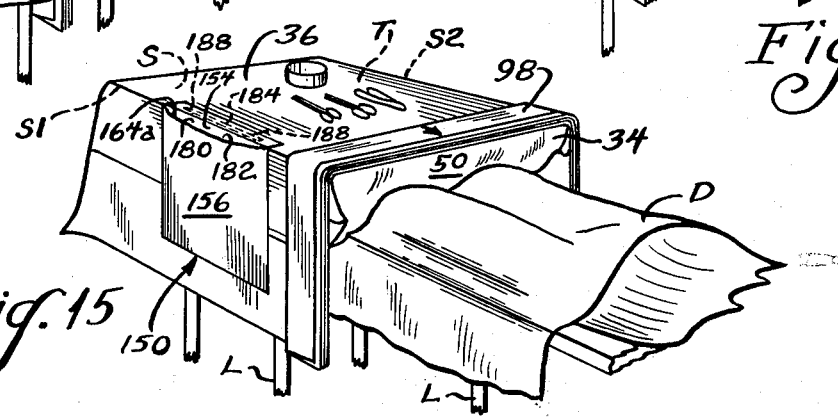

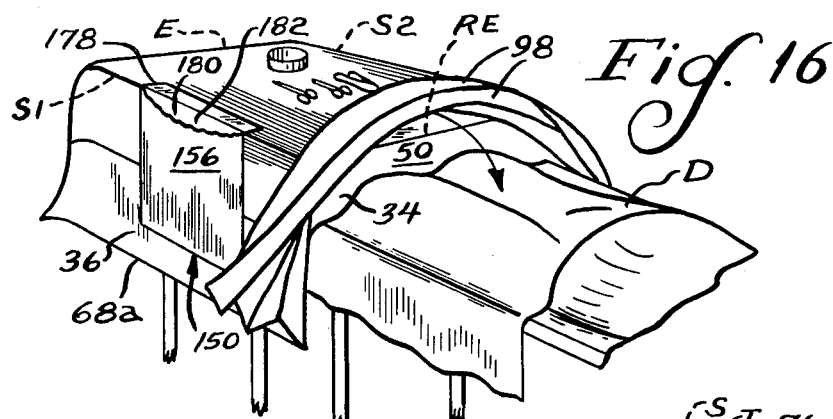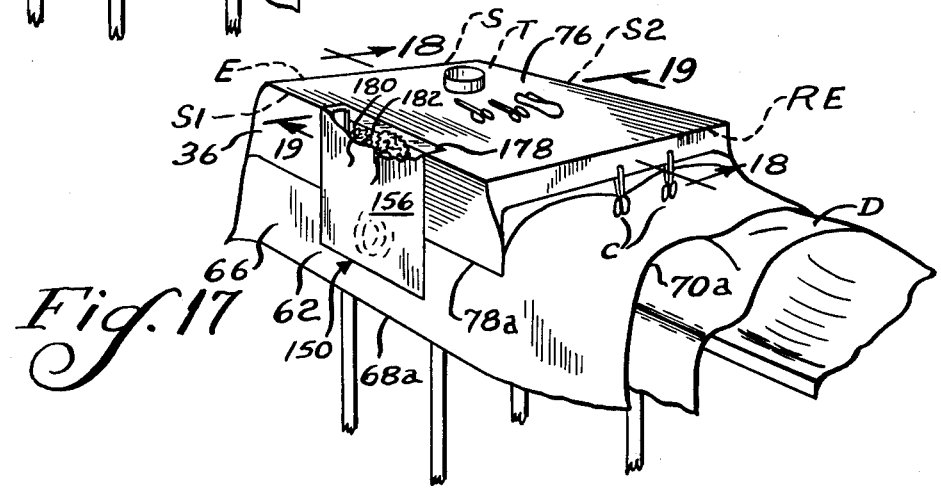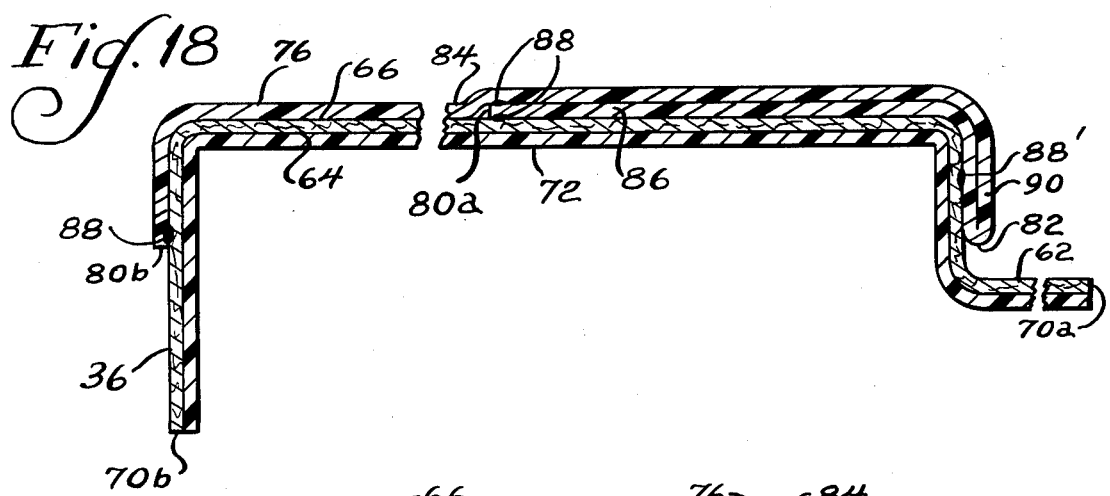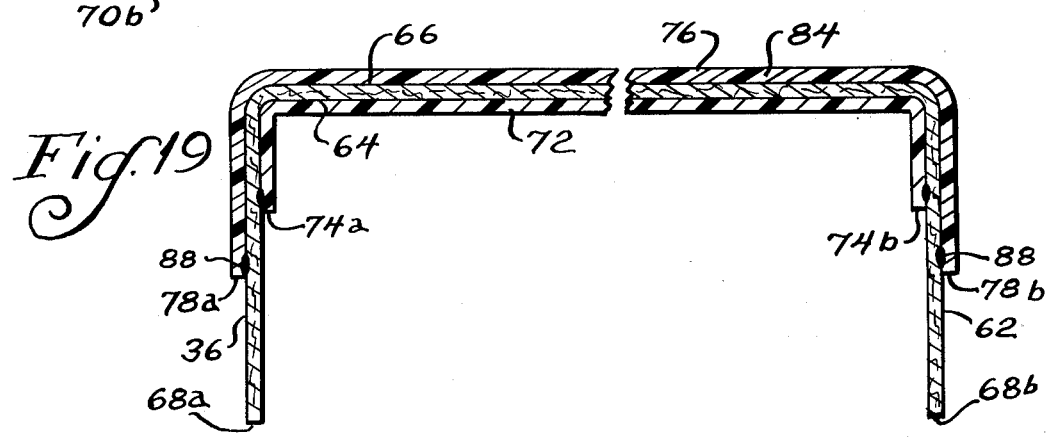

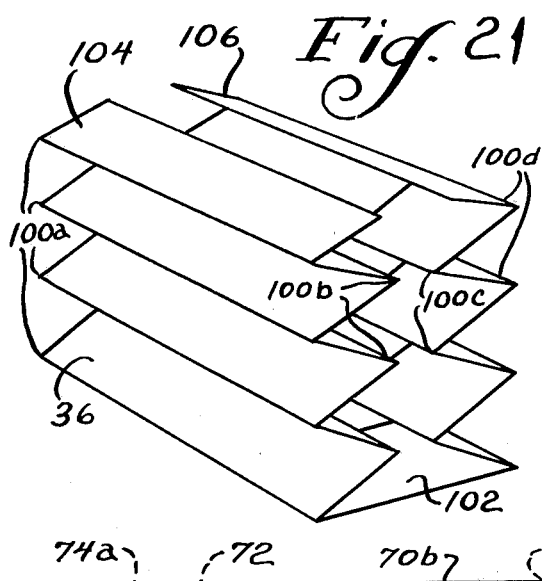
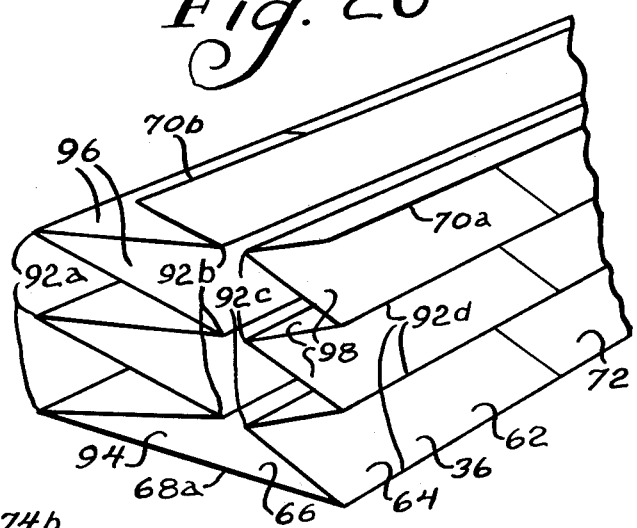
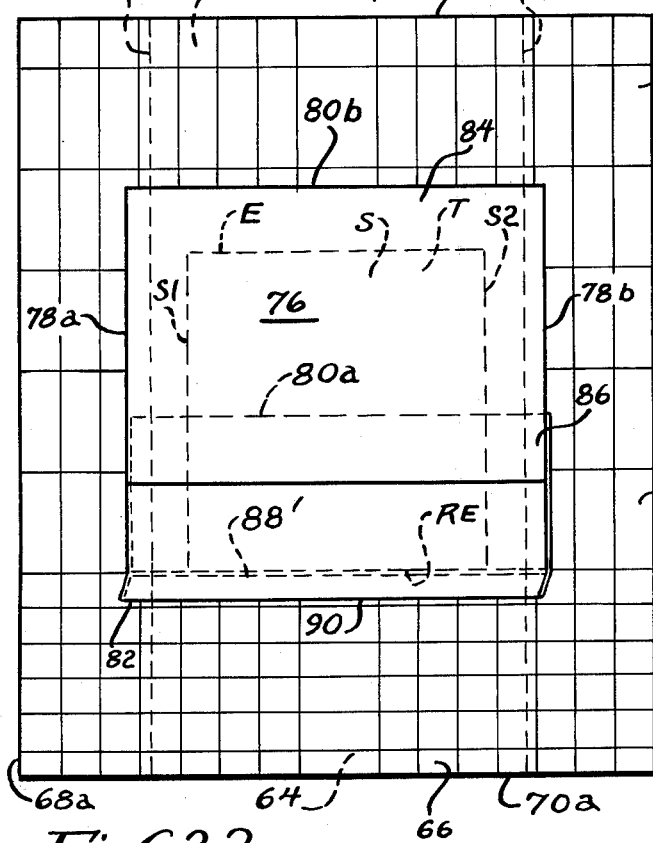
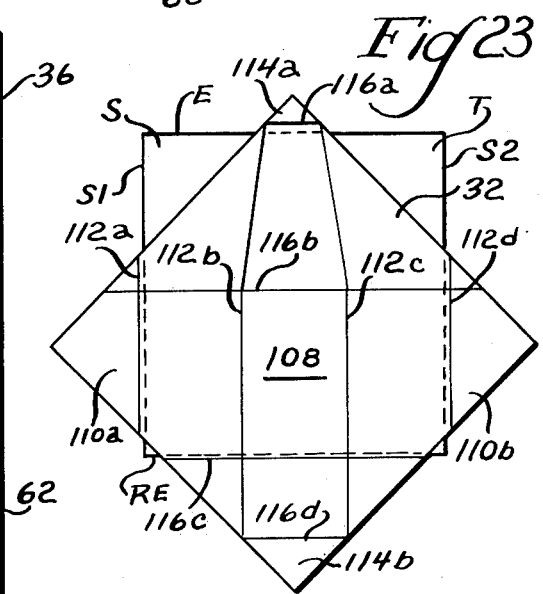
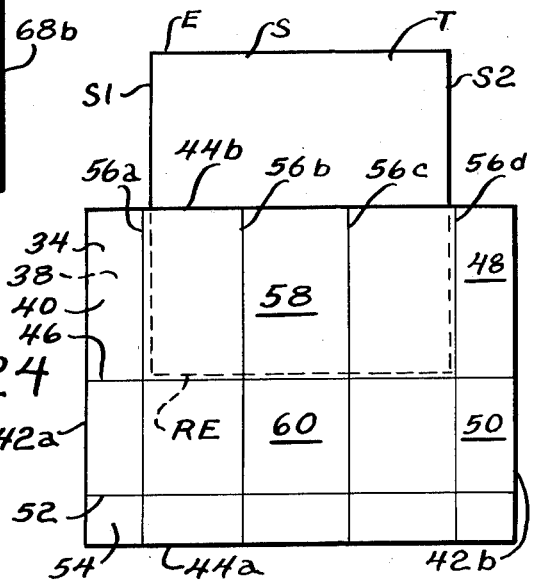

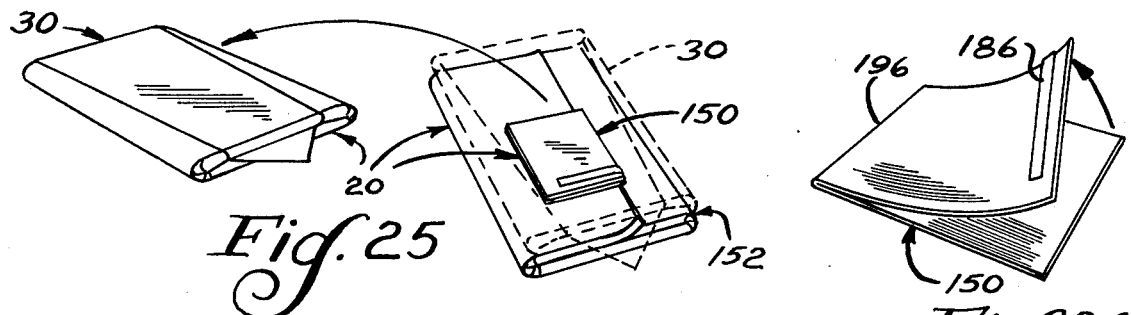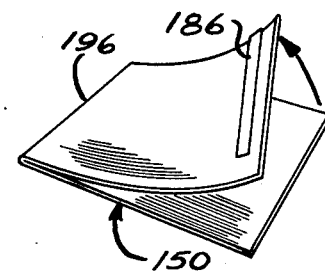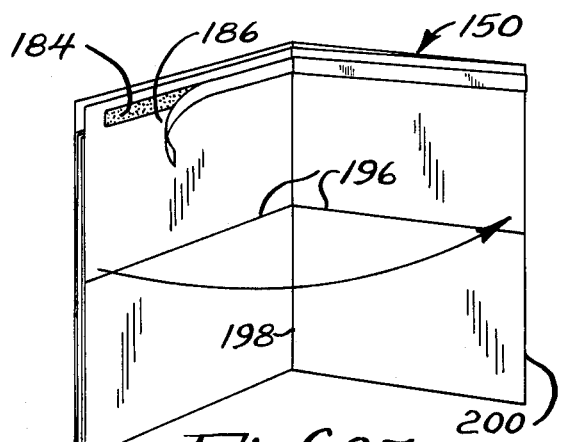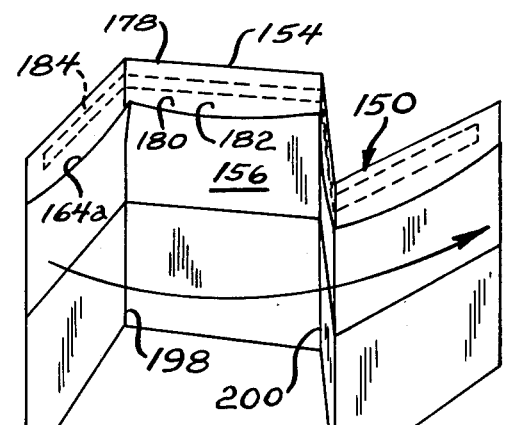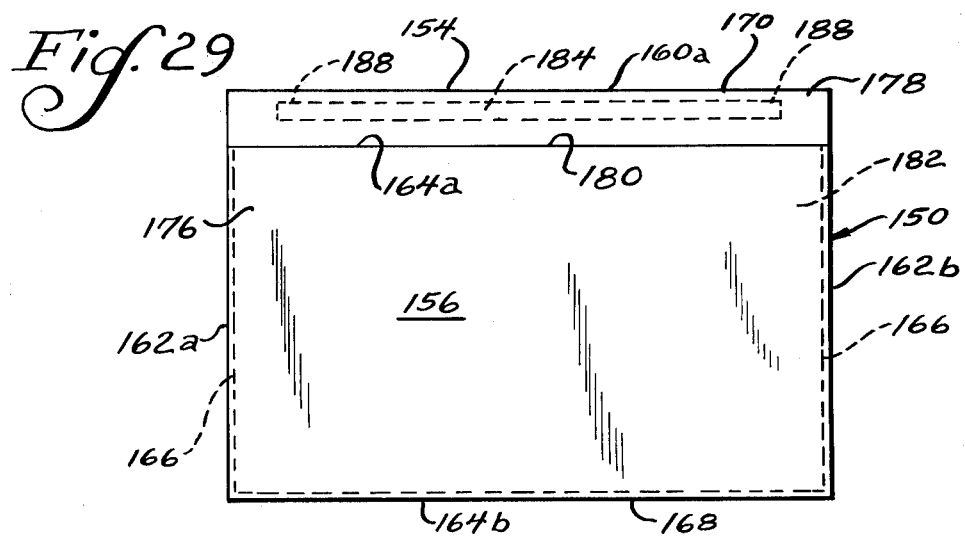

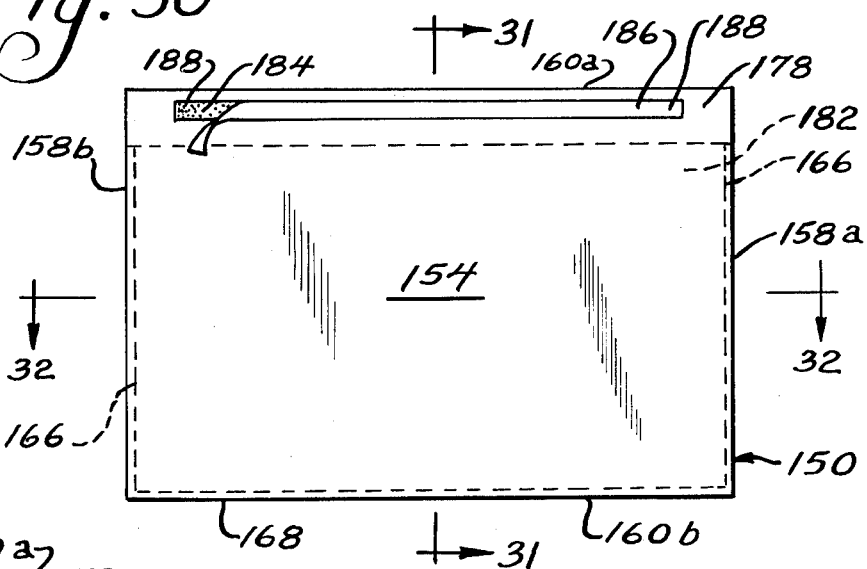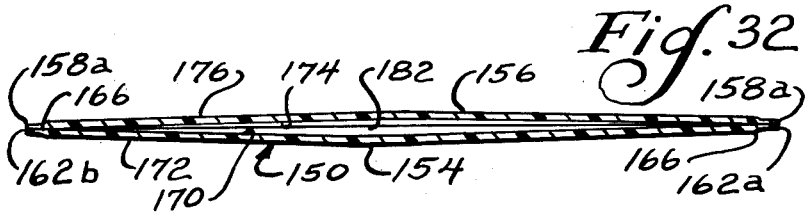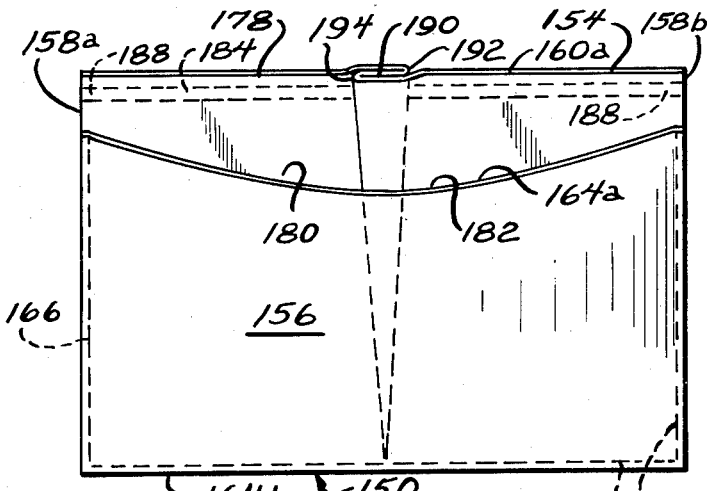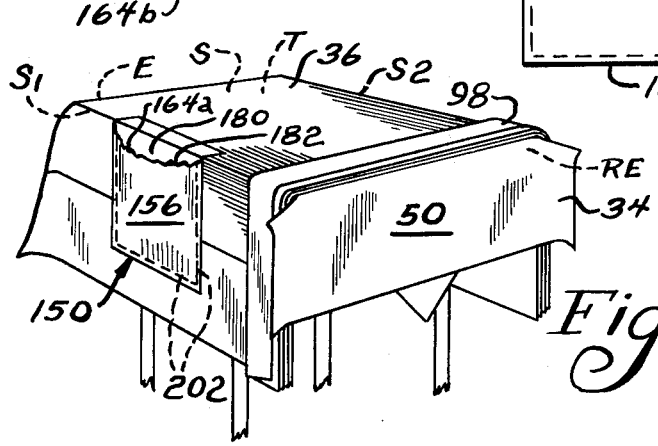

DRAPE ASSEMBLY WITH POUCH AND METHOD

CROSS REFERENCE TO RELATED APPLICATION

This application is a continuation-in-part of Ser. No. 664,136, filed March 5, 1976.

BACKGROUND OF THE INVENTION

The present invention relates to drapes, and more particularly to drapes for surgical equipment tables.

Tables are commonly used in the operating room to hold sterile articles, such as surgical instruments, during an operation. Such instrument tables are often constructed with a metal top or slab having a plurality of widely-spaced depending legs, and are arranged to modify the elevation of the table top in order that the table may be positioned over a patient with the patient being located between the spaced legs.

Since the table is non-sterile, it is necessary to cover the table with a sterile barrier prior to placement of the sterile articles on the table. Once drapes have been placed over both the table and the patient and after the table has been positioned adjacent the patient, the operation can commence. However, various articles, such as empty packages and sponges, must be discarded pursuant to the operation, and provision should be made for disposal of the refuse in a simplified manner. If such materials are placed on the table drape, they clutter the drape and make quick access to necessary articles, such as the instruments, more difficult.

SUMMARY OF THE INVENTION

A principal feature of the present invention is the provision vision of a drape assembly for covering a surgical equipment table and providing ready disposal of refuse pursuant to an operation.

The drape assembly of the present invention comprises, a sterile table drape which is unfolded for covering the equipment table. The drape assembly has a retaining pouch having front and back walls defining a pocket, and means for attaching the pouch to an outer surface of the drape adjacent a covered edge of the table.

A feature of the present invention is that the pouch permits disposal of refuse in a convenient and simplified manner.

Another feature of the invention is that the pouch maintains an opening communicating with the pocket in an open configuration to facilitate disposal of refuse into the pocket.

Yet another feature of the invention is that the pouch may be attached to the table drape in a simple and convenient manner.

Still another feature of the invention is that in an embodiment the pouch is retained on the drape for placement below a table edge when the table drape is unfolded over the table.

Further features will become more fully apparent in the following description of the embodiments of this invention and from the appended claims.

DESCRIPTION OF THE DRAWINGS

In the drawings:

FIGS. 1–17 are perspective views illustrating steps during placement of a folded drape assembly on an equipment table with FIGS. 14–17 showing placement of a refuse pouch on a table drape;

FIG. 18 is a fragmentary sectional view of the table drape taken substantially as indicated along the line 18—18 of FIG. 17;

FIG. 19 is a fragmentary sectional view of the table drape taken substantially as indicated along the line 19—19 of FIG. 17;

FIG. 20 is a fragmentary perspective view illustrating the manner in which the table drape is laterally fan folded;

FIG. 21 is a perspective view illustrating the manner in which the laterally folded table drape is transversely fan folded;

FIG. 22 is a plan view of the table drape;

FIG. 23 is a plan view of a cover sheet for the drape assembly;

FIG. 24 is a plan view of a set-up drape for the drape assembly;

FIG. 25 is a perspective view of a drape assembly including the refuse pouch;

FIGS. 26–28 are perspective views illustrating steps during placement of the refuse pouch of the present invention;

FIG. 29 is a front plan view of the refuse pouch of the present invention;

FIG. 30 is a back plan view of the refuse pouch of the present invention;

FIG. 31 is a sectional view taken substantially as indicated along the line 31—31 of FIG. 30;

FIG. 32 is a sectional view taken substantially as indicated along the line 32—32 of FIG. 30;

FIG. 33 is a front plan view of another embodiment of a refuse pouch of the present invention; and FIG. 34 is a perspective view of a table drape of the present invention showing a pouch for retention of refuse.

DESCRIPTION OF THE PREFERRED EMBODIMENTS

Referring now to FIG. 25, there is shown a drape assembly or pack generally designated 20 having a folded table drape assembly generally designated 30, a folded refuse pouch generally designated 150, and any other suitable folded drape or drapes generally designated 152, such as a drape for placement over a patient during an operation.

Figure 1:
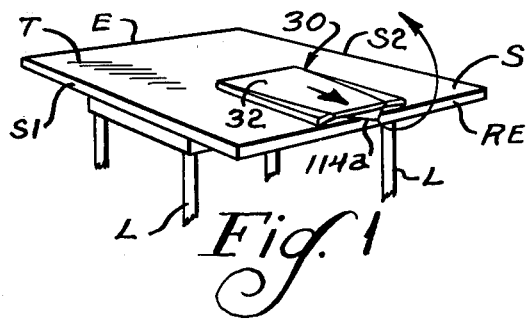

With reference to FIG. 1, the table drape assembly 30 is removed from the pack 20 and is positioned on a surgical equipment table T, such as an equipment table sold by Phelan Manufacturing Corporation commonly used in an operating room to hold surgical instruments or other sterile articles during a surgical procedure or operation. A table of this type has a metal top or slab S, and a plurality of widely spaced depending legs L for supporting the table slab S. The elevation of the table slab S may be adjusted by suitable means (not shown) in order that the table may be positioned over a patient with the patient located intermediate the legs L to place the instruments and articles at a convenient location for use during the operation. The metal table slab S has a plurality of edges and relatively sharp corners at the juncture of the edges. For convenience in discussion only, two opposed edges of the table will be termed end edges, and the other opposed edges will be termed side edges, with a reference end edge being designated RE, an end edge remote the reference edge RE being designated E, and the side edges connecting the reference and remote edges RE and E being designated S1 and S2.

As shown in FIGS. 29-32, the refuse pouch 150 has a first sheet 154 of a flexible material defining a back wall of the pouch, and a second sheet 156 of a flexible material defining a front wall of the pouch. The sheets 154 and 156 are preferably made of a durable liquid resistant material, such as Tyvek, a trademark of E. I. du Pont de Nemours. The first sheet 154 has a pair of side edges 158a and b, an inner surface 170, and an outer surface 172. The second sheet 156 has a pair of side edges 162a and 162b, a pair of end edges 164a and 164b connecting the side edges 162a and b, an inner surface 174, and an outer surface 176. The side edges of the first and second sheets 154 and 156 may be joined together by any suitable means, such as by lines of adhesive 166 extending along the side edges of the pouch, as shown. The pouch may be constructed from separate sheets with the lower end edges 160b and 164b being attached together, or from a single sheet which is folded in order to define edges of the sheet. Thus, as shown in FIG. 31, a single sheet may be folded along a fold line 168 in order to define the lower end edges 160b and 164b of the first and second sheets.

With reference to FIGS. 29-32, the upper end edge 164a of the second sheet 156 is spaced below the upper end edge 160a of the first sheet 154, thus defining an upper flap 178 of the first sheet 154 extending laterally between the side edges 158a and b of the first sheet 154. Also, the upper edge 164a of the second sheet 156 defines an opening 180 which communicates with a pocket 182 located intermediate the first and second sheets 154 and 156, respectively, and between the joined side edges and lower end edges of the sheets. As shown, the upper flap 178 of the pouch 150 has an elongated strip of pressure-sensitive adhesive 184 on the outer surface 172 which extends along the upper edge 160a of the first sheet 154 and which may comprise a double face tape having a core with adhesive on each side. A release sheet 186 is releasably attached to the adhesive strip 184 in order to cover the adhesive until ready for use. As shown in FIGS. 29 and 30, opposed ends 188 of the adhesive strip 184 are spaced from the side edges 158a and b of the first sheet 154 for a purpose which will be described below.

Another embodiment of the pouch 150 of the present invention is illustrated in FIG. 33, in which like reference numerals designate like parts. In this embodiment, the lower end edges of separate sheets 154 and 156 are joined together by adhesive 166, and the first sheet 154 has a pleat 190 defined by a pair of fold lines 192 and 194 which extend from the upper end edge 160a of the first sheet. The pleat 190 may be secured together by suitable means, such as by adhesive or the adhesive strip core, and the opposed ends 188 of the adhesive strip 184 may extend to the side edges 158a and b of the first sheet 154, if desired. Due to the pleat 190, the width of the second sheet 156 at the edge 164a is greater than the width of the pleated first sheet 154, which may also be accomplished by selecting the relative widths of the sheets without pleating. As a result, the pouch causes the second sheet 156 to gap away from the first sheet 154 at the edge 164a in order to maintain a relatively large opening 180 for easy disposal of refuse into the pouch pocket 182. As will be seen below, this result is also accomplished in the pouch of FIGS. 29-32 by spacing the opposed ends 188 of the adhesive strip 184 from the side edges of the first sheet.

Figure 6:
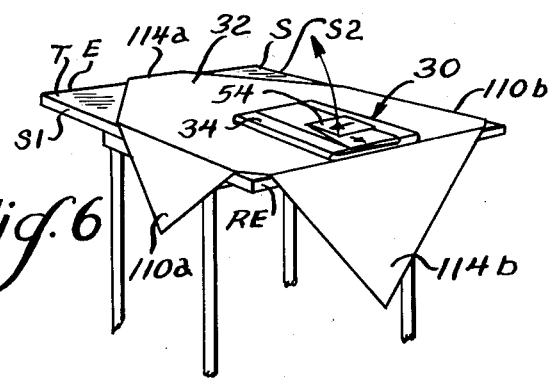

As illustrated in FIGS. 1 and 23, the folded drape assembly 30 has an outer cover sheet 32 which is made of a material resistant to passage of bacteria, such as a cellulosic or nonwoven material. As illustrated in FIGS. 6 and 24, the folded drape assembly 30 has a sterile set-up drape 34 which is also made of a material resistant to passage of bacteria, such as a cellulosic or nonwoven material. As shown in FIGS. 10 and 22, the folded drape assembly 30 further has a sterile table drape 36.

Referring to FIG. 24, the set-up drape 34 has a first surface 38 facing the table T when the set-up drape is placed, a second surface 40 facing away from the table T when the drape is placed, a pair of side edges 42a and 42b, and a pair of end edges 44a and 44b connecting the side edges 42a and b. The set-up drape 34 has a lateral fold line 46 defining a retaining panel 48 and a barrier panel 50, with the retaining panel 48 being defined by the fold line 46, the side edges 42a and b, and the end edge 44b, and with the barrier panel 50 being defined by the fold line 46, the side edges 42a and b, and the end edge 44a. As shown, the barrier panel 50 has a lateral fold line 52 extending between the side edges 42a and b and defining a laterally extending grasping panel 54. The set-up drape 34 also has a plurality of transverse fold lines 56a, 56b, 56c, and 56d defining a plurality of transverse sections, including a lateral central section 58 in the retaining panel 48, a lateral central section 60 in the barrier panel 50, and a plurality of sections intermediate the central sections 58 and 60 and the side edges 42a and 42b of the set-up drape or sheet.

Referring to FIGS. 17-19, and 22, the table drape 36 has a main sheet 62 which is made of a material resistant to passage of bacteria, such as a nonwoven material which is preferably treated to provide for liquid repellency. The main sheet 62 has a first surface 64 facing toward the table T when the table drape is placed, a second surface 66 facing away from the table T when the table drape is placed, a pair of side edges 68a and 68b, and a pair of end edges 70a and 70b connecting the side edges 68a and b.

As illustrated in FIGS. 18, 19, and 22, the table drape 36 has a sheet 72 of liquid impervious material, such as polyethylene, extending between the end edges 70a and b of the main sheet 62. As shown in FIGS. 19 and 22, the liquid impervious sheet 72 has a pair of side edges 74a and 74b spaced from the side edges 68a and 68b of the main sheet 62, with the width of the liquid impervious sheet 72 between its side edges 74a and b being sufficient to extend past the side edges of the table T when the table drape is properly placed on the table. The liquid impervious sheet 72 is secured to the first surface 64 of the main sheet 62 and defines the undersurface of the table drape when the unfolded table drape is placed on the table.

Referring to FIGS. 17-19, and 22, the table drape 36 also has a protective sheet 76 which is made of a material resistant to abrasion and passage of liquid, such as Tyvek, a trademark of E. I. duPont de Nemours. The protective sheet 76 has a pair of side edges 78a and 78b, and a pair of end edges 80a and 80b connecting the side edges 78a and b, with the width between the side edges 78a and b of the protective sheet 76 being sufficient for the protective sheet to extend past the side edges of the table T when the unfolded drape is placed on the table. As shown in FIGS. 18 and 22, the protective sheet 76 has a fold line 82 defining a cover section 84 extending between the fold line 82 and the end edge 80b, and an end section 86 extending between the fold line 82 and the end edge 80a, such that the end section 86 is folded beneath the cover section 84 to form a doubled end portion of the protective sheet 76. The protective sheet 76 is secured to the second surface 66 of the main sheet 62 in this configuration by suitable means, such as by lines of adhesive 88, including a line of adhesive 88' which is spaced slightly from the fold line 82 of the protective sheet 76. Thus, the doubled protective sheet 76 defines an upper surface of the table drape 36 when the unfolded drape is placed on the table, with the length of the cover sheet 84 between the fold line 82 and the end edge 80b being sufficient to extend past the end edges of the table T. Also the line of adhesive 88' defines a free clip panel 90 of doubled material adjacent the fold line 82 for a purpose which will be described below.

Referring to FIG. 20, the table drape 36 has a plurality of lateral fold lines 92a, 92b, 92c, and 92d extending between the side edges of the main sheet 62, with the fold lines 92a and 92d defining a laterally extending central panel 94, with the fold lines 92a and 92b defining a first set of lateral fan or accordion folds 96, and with the fold lines 92c and 92d defining a second set of lateral fan or accordion folds 98. As shown, the first and second sets of lateral fan folds 96 and 98, respectively, are folded over the second surface 66 of the central panel 94, with the distance between the fold lines 92a and 92b in the first set of fan folds 96 being greater than the distance between the fold lines 92c and 92d in the second set of fan folds 98 to provide additional material in the first set of fan folds 96 for a purpose which will be described below. In the laterally folded configuration, the fold lines 92b and 92c of the lateral fan folds define inner edges of the fan folds which abut each other in the drape, and the fold lines 92a and 92d define outer edges of the first and second sets of fan folds. Also, the sets of fan folds 96 and 98 have laterally extending panels at their outer ends adjacent the end edges 70b and 70a which are convenient for grasping during placement of the table drape.

Referring to FIG. 21, the laterally folded table drape 36 has a plurality of transverse fold lines 100a, 100b, 100c, and 100d defining a transverse central panel 102, a first set of transverse fan folds 104, and a second set of transverse fan folds 106, with the first and second sets of transverse fan folds 104 and 106, respectively, being folded over the outer ends of the lateral fan folds in the transverse central panel 102. In this configuration, the outer ends of the transverse fan folds 104 and 106 define transverse panels for convenient grasping during placement of the drape.

With reference to FIG. 24, the transversely folded table drape is positioned on the central section 58 of the set-up drape retaining panel 48 with the outer ends of the transverse fan folds facing away from the second surface 40 of the set-up drape 34. Next, the barrier panel 50 is folded over the table drape along the fold line 46, and the grasping panel 54 is folded back along the fold line 52. Finally, the side sections of the set-up drape defined by the transverse fold lines 56a, b, c, and d are folded over the central section 60 of the barrier panel 50 to cover the folded table drape with the folded set-up drape.

With reference to FIG. 23, the folded table and set-up drapes are positioned on a central section 108 of the cover sheet 32, side portions 110a and 110b of the cover sheet 32 are folded inwardly along transverse fold lines 112a, 112b, 112c, and 112d, after which end portions 114a and 114b of the cover sheet 32 are folded inwardly along lateral fold lines 116a, 116b, 116c, and 116d. In this manner, the folded set-up drape is covered by the cover sheet.

Referring again to FIGS. 1 and 25, the use of the folded drape assembly 30 is described as follows. Initially, drape assembly 20 is retained in a package (not shown) of a material resistant to passage of bacteria, such as polyethylene, and the drape assembly 20 is sterilized within the package. When ready for use, the protective package is opened by a non-sterile person in the operating room, such as a circulating nurse, who removes the drape assembly 30 from the assembly 20 while grasping the cover sheet 32 which permits handling of the drape assembly by non-sterile hands without contamination of the covered set-up and table drapes. Referring to FIG. 1, the circulating nurse places the folded drape assembly on the table top or slab S with a designated edge of the drape assembly aligned with the reference edge RE and with the assembly located generally centrally between the side edges S1 and S2 of the table T. The proper placement for the edge of the drape assembly is indicated by the indicia or printed arrow on the outside of the cover sheet 32, as shown. As will be seen below, in this reference position of the assembly, the fold line 46 of the set-up drape 34 (FIG. 24) and the outer edges of the second set of lateral fan folds 98 defined by fold lines 92d (FIG. 20) are located adjacent the reference edge RE of the table.

Figure 2:
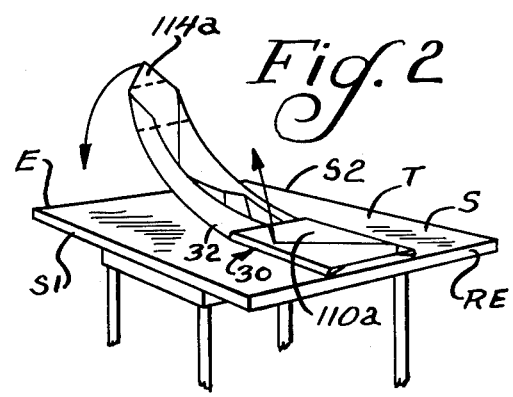
Figure 3:
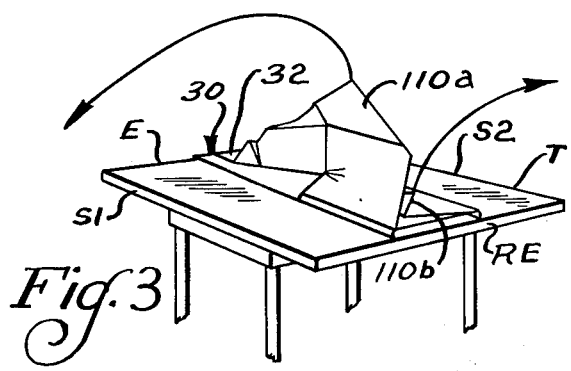
Figure 4:
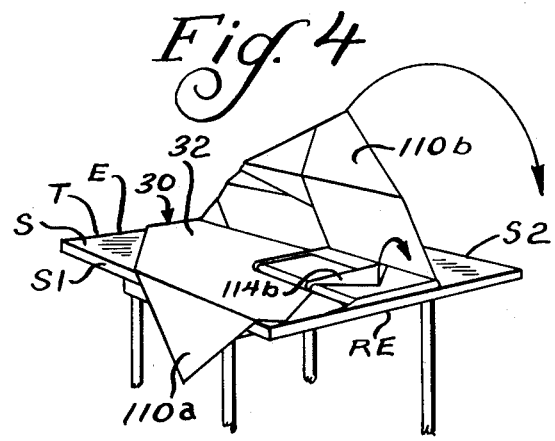
Figure 5:
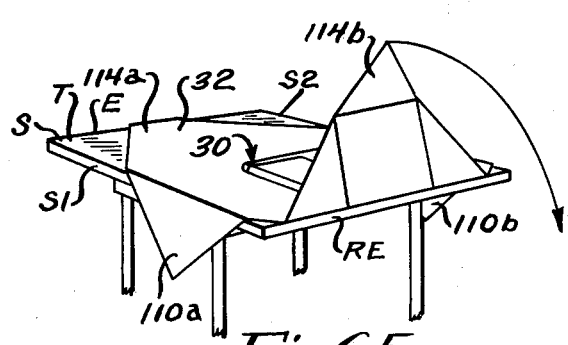

Referring to FIG. 1, the circulating nurse grasps the end portion 114a of the cover sheet 32, and, as shown in FIG. 2, unfolds the end portion 114a of the cover sheet 32 towards the remote edge E of the table T. Next, with reference to FIGS. 2 and 3, the circulating nurse grasps the side portion 110a of the cover sheet 32, and unfolds the side portion toward the side edge S1 of the table T. As illustrated in FIGS. 3 and 4, the circulating nurse then grasps the other side portion 110b of the cover sheet 32, and unfolds this side portion toward the side edge S2 of the table. Finally, as illustrated in FIGS. 4 and 5, the circulating nurse grasps the other end portion 114b of the cover sheet 32, and unfolds the end portion 114b over the reference edge RE, after which the end portion 114b of the cover sheet 32 depends below the reference edge RE, as shown in FIG. 6. (The configuration of the unfolded cover sheet 32 relative the table size is illustrated in FIG. 23.) Thus, the folded set-up drape 34 has been exposed adjacent the reference edge RE of the table T without contamination of the set-up drape by the non-sterile hands of the circulating nurse.

Figure 7:
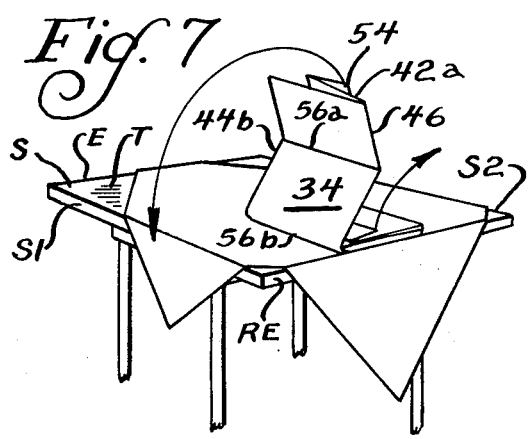
Figure 8:
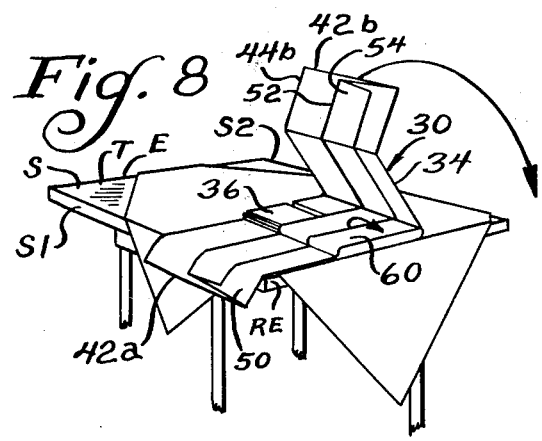

At this time, a sterile person in the operating room, such as a scrub nurse, unfolds the sterile set-up drape 34 in the following manner. With reference to FIGS. 6 and 7, the scrub nurse grasps the grasping panel 54 in one side portion of the set-up drape 34, and unfolds the side portion toward the side edge S1 of the table, after which she grasps the grasping panel 54 in the other side portion of the set-up drape 34 and unfolds it toward the other side edge S2 of the table T, as shown in FIGS. 7 and 8. Next, as illustrated in FIGS. 8 and 9, the scrub nurse grasps the grasping panel 54 in the central section 60 of the barrier panel 50, and unfolds the barrier panel 50 from the drape assembly 30 into a configuration with the barrier panel 50 extending a substantial distance below the reference edge RE of the table T, as shown in FIG. 10. (The configuration of the unfolded set-up drape 34 relative the table size is illustrated in FIG. 24.) With reference to FIG. 10, the set-up drape 34 has a sufficient width between the side edges 42a and b to extend past the side edges S1 and S2 of the table T, such that the unfolded set-up drape 34 covers the entire reference edge RE of the table including the corners of the table at the juncture of the side edges S1 and S2 and the reference edge RE. Thus, the unfolded set-up drape 34 exposes the table drape 36 without contamination of the table drape, and the unfolded set-up drape 34 forms a sterile barrier along the reference edge RE of the table to prevent contamination of the sterile nurse by the non-sterile table during placement of the table drape 36. The weight of the table drape 36 on the retaining panel 48 of the set-up drape 34 retains the set-up drape at its barrier position.

The sterile table drape 36 is unfolded by the sterile scrub nurse in the following manner. First, with reference to FIGS. 10 and 11, the transverse fan folds 104 are unfolded from the assembly 30 into a configuration with side portions of the table drape extending past the side edge S1 of the table, after which the transverse fan folds 106 of the table drape are unfolded from the assembly 30 into a configuration with side portions extending past the side edge S2 of the table T, as shown in FIGS. 12 and 13, such that the side portions of the partially unfolded table drape 36 extend a substantial distance below the respective side edges S1 and S2 of the table. Next, as illustrated in FIG. 13, the set of lateral fan folds 96 of the table drape 36 are unfolded toward the remote edge E of the table T, such that an end portion of the table drape is unfolded from the assembly into a configuration extending a substantial distance below the remote table edge E, as best shown in FIG. 14. In this configuration, the partially unfolded table drape 36 provides a sterile barrier for the table around its edges S1, E, and S2, while the barrier panel 50 of the set-up drape 34 continuously provides a sterile barrier along the table reference edge RE. The second set of fan folds 98 of the table drape 36 remains in a folded configuration for later use, as described below.

The pouch 150 of the present invention may be attached to the outer surface of the table drape 36 at this time. With reference to FIGS. 25 and 26, the pouch 150 is removed from the drape assembly 20, and is unfolded about a fold line 196 which extends laterally relative the side edges of the pouch. Next, as shown in FIG. 27, the pouch 150 is unfolded about fold lines 198 extending between end edges of the pouch, and the release sheet 186 may be peeled from the adhesive strip 184 in order to expose the adhesive for subsequent use. As shown in FIG. 28, the pouch is then unfolded along a central fold line 200 extending between the end edges of the pouch, such that the pouch 150 has been completely unfolded with the adhesive exposed on the outer surface of the flap 178 and with the pouch opening 180 exposed for access to the pouch pocket 182.

Referring to FIG. 14, the pouch 150 may be attached to the outer surface of the drape by pressing the flap 178 against the table adjacent the side edge S1 of the table T and above the table top S. Thus, the adhesive 184 retains the flap 178 against the drape in an overlying relationship with the table top, and with the lower portion of the pouch 150 depending along the side portions of the table drape 36 below the table edge S1, as shown in FIG. 15. Since the opposed ends 188 of the adhesive strip 184 are spaced from the side edges of the pouch, the side margins of the pouch are permitted to move slightly outwardly relative the table, thus permitting the end edge 164a of the second sheet 156 to gap away from the first sheet 154 and maintain the opening 180 of the pouch 150 relatively large for ready disposal of refuse into the pocket 182. As previously indicated, the same result is achieved by the pouch described in connection with FIG. 33.

With reference to FIG. 34, in another embodiment, the sheet 156 is attached directly to the table drape 36 by suitable means, such as by a line of adhesive 202 which extends along the side edges and the lower end edge of the sheet 156. The pouch 150 is located on the drape such that it will be positioned below the side edge S1 of the table T, or other edge, as desired, when the table drape 36 is unfolded during placement, as previously described. In a preferred form, the upper edge 164a of the sheet 156 has a greater length than the width of the drape as measured between the point at which the upper part of the sheet side edges are attached to the drape. In this manner, the upper edge 164a of the sheet 156 gaps away from the table drape 36 when placed on the table in order to maintain the opening 180 relatively large for easy access to the pocket 182 in the pouch 150.

Referring to FIG. 15, sterile articles, such as surgical instruments, are placed on the unfolded portion of the table drape 36 covering the table top S, and the patient is prepared for the operation, including placement of a drape on the patient in a separate draping procedure. As before, the barrier panel 50 of the set-up drape 34 provides a sterile barrier for the reference edge RE of the table during placement of instruments on the table drape 36 and while moving the table. When the patient has been properly prepared for the operation, the table T may be positioned over the patient, e.g., his legs, with the patient located intermediate the legs L of the table T, as shown in FIG. 15. Since the barrier panel 50 of the set-up drape 34 passes over the patient's feet, the barrier panel 50 may become contaminated by the patient or by the operating room table as the table is being positioned over the patient. However, as illustrated in FIG. 16, the second set of lateral fan folds 98 may be unfolded by the sterile scrub nurse into a configuration over the barrier panel 50 of the set-up drape 34, such that the unfolded second set of lateral fan folds forms a continuous sterile barrier with a sterile drape D previously placed over the patient, as illustrated in FIG. 17. At this time, the table has been positioned near the surgical site for convenient use of the surgical instruments on the sterile table drape, and the unfolded table drape 36 provides a sterile barrier completely around the sides of the table, including the reference edge RE which is positioned adjacent the surgical site. If desired, the pouch 150 may be attached to the table drape after the table drape has been fully unfolded.

It will be seen that the cover sheet permits handling of the folded drape assembly by non-sterile hands, and the folded assembly is positioned adjacent a reference edge of the instrument table. The unfolded barrier panel of the sterile set-up drape provides a sterile barrier for the reference edge of the table while the table drape is partially unfolded to cover a substantial portion of the table and while articles are placed on the table. After the instruments have been placed on the table, the table is positioned over the patient and the remaining portion of the table drape is unfolded to provide a sterile barrier over the lower part of the set-up drape. Thus, the drape assembly permits the table to be covered in an aseptic and simplified manner.

With reference to FIG. 17, the pouch 150 provides a convenient container for disposal of refuse, such as empty packages and sponges, which may be discarded before, during, or after the operation. The pouch 150 of the present invention is attached in a simplified manner to the table drape 36, and permits the top of the table drape to remain free of obstruction which otherwise might be caused by placement of such materials on the drape.

According to a method of the present invention the equipment table is covered by positioning a folded sterile table drape adjacent a reference edge of the table. Side portions of the drape are unfolded to a location extending substantially below opposed edges of the table adjacent the reference edge. A first end portion of the drape is unfolded to a location extending substantially below an edge of the table remote the reference edge. A second end portion of the drape is unfolded to a location below the reference table edge, and a pouch is attached to an outer surface of the drape adjacent a covered table edge. As previously indicated, the attaching step may occur between the last two unfolding steps.

According to another method of the present invention the equipment table is covered by positioning a folded sterile table drape adjacent a reference edge of the table. Side portions of the drape are unfolded to a location extending substantially below opposed edges of the table adjacent the reference edge while positioning a pouch on a side portion of the drape below an opposed edge of the table. A first end portion of the drape is unfolded to a location extending substantially below an edge of the table remote the reference edge, and a second end portion of the drape is unfolded to a location below the reference table edge.

The configuration of the unfolded table drape 36 relative the table size is illustrated in FIG. 22. As shown, the protective sheet 76 of the placed table drape 36 extends past the edges S1, E, S2, and RE of the table. The durable material of the protective sheet 76 resists puncturing of the table drape 36 by sharp corners of the table at the juncture of the table side and end edges, and provides a cushion for the instruments which are dropped onto the table during the operation to prevent puncturing of the table drape 36 by the instruments. The portion of the unfolded table drape located over the table top S adjacent the reference edge RE is subject to the most abuse during the operation, since the reference edge RE of the table is located nearest the surgical site. Consequently, instruments are repeatedly dropped upon and removed from this portion of the table, and operating room personnel brush against and apply pressure to this part of the drape. The doubled portion of the protective sheet 76 provides additional resistance against abrasion of the drape by the instruments and pressure exerted against the table corners to prevent puncturing of the table drape 36 which otherwise would result in loss of the sterile barrier over the table.

With reference to FIGS. 17, 18, and 22, the clip panel 90 of the protective sheet 76 is located slightly below the reference edge RE of the table T when the unfolded table drape 36 has been properly placed on the table T. Thus, the clip panel 90 provides a convenient medium on which clips C, such as towel clips, may be attached during the operation, and provides a strong segment of the drape on which other items, such as aspiration tubing, cautery cord, etc., may be attached in a convenient manner. Since both opposed surfaces of the clip panel 90 are sterile, the sterile barrier over the table is not lost when the clips should puncture the clip panel 90.

With reference to FIGS. 17-19, and 22, the protective sheet 76 is resistant to passage of liquid, and the liquid impervious sheet 72 and the protective sheet 76 provide a barrier to prevent passage of liquid through the table drape 36 during the operation, which otherwise might result in loss of the sterile barrier.

The foregoing detailed description is given for clearness of understanding only, and no unnecessary limitations should be understood therefrom, as modifications will be obvious to those skilled in the art.

I claim:

1. A disposable drape assembly, comprising:
   a sterile drape comprising a sheet of flexible material; and
   a retaining pouch initially separated from said drape and having a back wall comprising a sheet of flexible material, a front wall comprising a sheet of flexible material, with said sheets defining a pocket and an opening for placement of articles in the pouch, and means for attaching the pouch to the drape at a selected location after placement of the drape with the back wall facing the drape.

2. The assembly of claim 1 wherein the back wall includes a flap extending beyond an upper edge of the front wall, and in which the attaching means is located on said flap.

3. The assembly of claim 1 wherein the back wall includes an upper edge, and in which the attaching means is located on an outer surface of the back wall adjacent said upper edge.

4. The assembly of claim 3 wherein the attaching means is spaced from side edges of the pouch.

5. The assembly of claim 4 wherein said attaching means comprises a strip of pressure-sensitive adhesive extending along the upper edge of the back wall.

6. The assembly of claim 1 wherein the back wall includes an upper edge and a pleat extending from said upper edge.

7. The assembly of claim 1 wherein the width of the back wall is greater than the width of the front wall adjacent said opening.

8. The assembly of claim 1 wherein the attaching means comprises a pressure-sensitive adhesive, and including a release sheet releasably attached to the adhesive.

9. A drape assembly for a surgical equipment table, comprising:
   a sterile folded table drape having side portions unfoldable from the drape into a configuration extending past opposed edges of the table adjacent a reference edge of the table, a first end portion unfoldable from the drape into a configuration extending substantially below an edge of the table remote the reference edge, and a second end portion unfoldable from the drape into a configuration extending below the table reference edge; and
   a retaining pouch having front and back walls defining a pocket and an opening communicating with the pocket, and means for attaching the pouch to the table drape with the opening located adjacent an edge of the table.

10. A drape assembly for a surgical equipment table comprising, a sterile folded table drape having side portions unfoldable from the drape into a configuration extending past opposed edges of the table adjacent a reference edge of the table, a first end portion unfoldable from the drape into a configuration extending substantially below an edge of the table remote the reference edge, a second end portion unfoldable from the drape into a configuration extending below the table reference edge, and a pouch positioned on an outer surface of the drape relative the table and defining a pocket for retaining articles therein, said pouch having an upper edge defining an opening communicating with the pocket adjacent a covered edge of the table.

11. The assembly of claim 10 wherein said pouch is attached to a side portion of said drape.

12. A method of covering a surgical equipment table in an aseptic manner, comprising the steps of:
 positioning a folded sterile table drape adjacent a reference edge of the table;
 unfolding side portions of the drape to a location extending substantially below opposed edges of the table adjacent the reference edge;
 unfolding a first end portion of the drape to a location extending substantially below an edge of the table remote the reference edge;
 unfolding a second end portion of the drape to a location below the reference table edge; and
 attaching a pouch to an outer surface of the drape adjacent a covered table edge.

13. The method of claim 12 wherein the attaching step is between the last two unfolding steps.

14. The method of claim 12 wherein the pouch is attached to a side portion of the drape adjacent an opposed edge of the table during the attaching step.

15. A method of covering a surgical equipment table in an aseptic manner, comprising the steps of:
 positioning a folded sterile table drape adjacent a reference edge of the table;
 unfolding side portions of the drape to a location extending substantially below opposed edges of the table adjacent the reference edge while positioning a pouch on a side portion of the drape below an opposed edge of the table; and
 unfolding a first end portion of the drape to a location extending substantially below an edge of the table remote the reference edge.

16. The method of claim 15 including the step of unfolding a second end portion of the drape to a location below the reference table edge.

* * * * *